Figure 1:
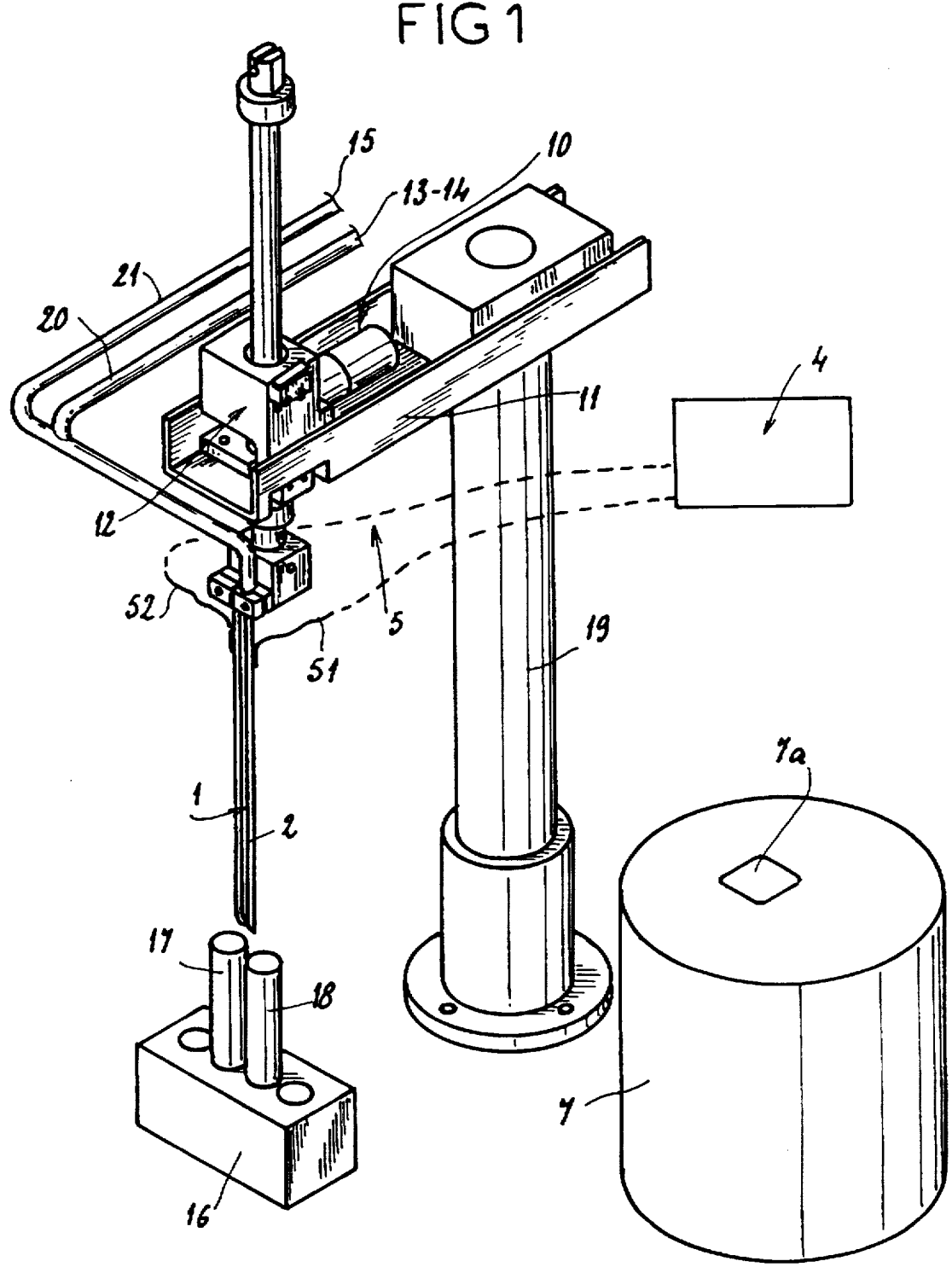

A United States Patent [19]
Colin et al.

[11] Patent Number: 5,765,490
[45] Date of Patent: Jun. 16, 1998

[54] DEVICE FOR WITHDRAWING AND/OR EJECTING A CONTAMINATING MEDIUM, WITH DECONTAMINATION OF THE MEMBER FOR MANIPULATING SAID MEDIUM

[75] Inventors: Bruno Colin, Marcy l'Etoile; Geneviève Bossy, Amberieu en Bugey, both of France

[73] Assignee: Bio Merieux, Marcy l'Etoile, France

[21] Appl. No.: 600,845

[22] Filed: Feb. 13, 1996

[30] Foreign Application Priority Data

Feb. 16, 1995 [FR] France ................................. 95 02010

[51] Int. Cl.$^6$ .......................................................... F23G 5/00
[52] U.S. Cl. ........................... 110/346; 110/250; 110/236; 219/635
[58] Field of Search ................................. 110/236, 250, 110/346; 422/22, 292; 219/68, 635, 636

[56] References Cited

U.S. PATENT DOCUMENTS

| | | | |
|---|---|---|---|
| 3,742,187 | 6/1973 | Folus | 422/22 X |
| 3,844,275 | 10/1974 | Elliott | 422/292 X |
| 5,075,529 | 12/1991 | Kudo | 219/635 X |
| 5,212,362 | 5/1993 | Burden et al. | 219/68 X |
| 5,277,868 | 1/1994 | Langford | 422/22 X |
| 5,300,752 | 4/1994 | Elmerick et al. | |
| 5,573,732 | 11/1996 | Waggener et al. | 422/22 X |

FOREIGN PATENT DOCUMENTS

| | | |
|---|---|---|
| 0 136 392 | 4/1985 | European Pat. Off. . |
| WO 92/14096 | 8/1992 | WIPO . |

Primary Examiner—William E. Tapoical
Assistant Examiner—Susanne C. Tinker
Attorney, Agent, or Firm—Oliff & Berridge, P.L.C.

[57] ABSTRACT

Process for heating a hollow needle (2) consisting essentially of a metal tube (3), the inside and/or outside of which have previously been brought into contact with a contaminating medium, according to which an electric current is supplied to the said needle, flowing in the metal wall and over the length of the said tube (3) and dissipating thermal energy therein through the ohmic effect, characterized in that a predetermined quantity of electrical energy is supplied to the said needle (2), metered as a function of the electrical characteristics of the said tube (3), on the one hand to suffice for decontamination of the needle, both inside and outside, and on the other hand to limit the heating and preserve the integrity, including the original shape, of the said needle.

17 Claims, 3 Drawing Sheets

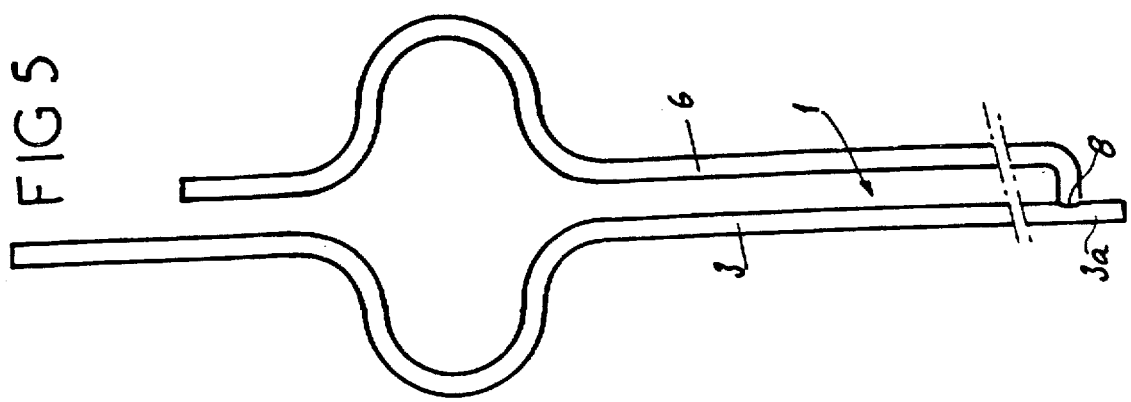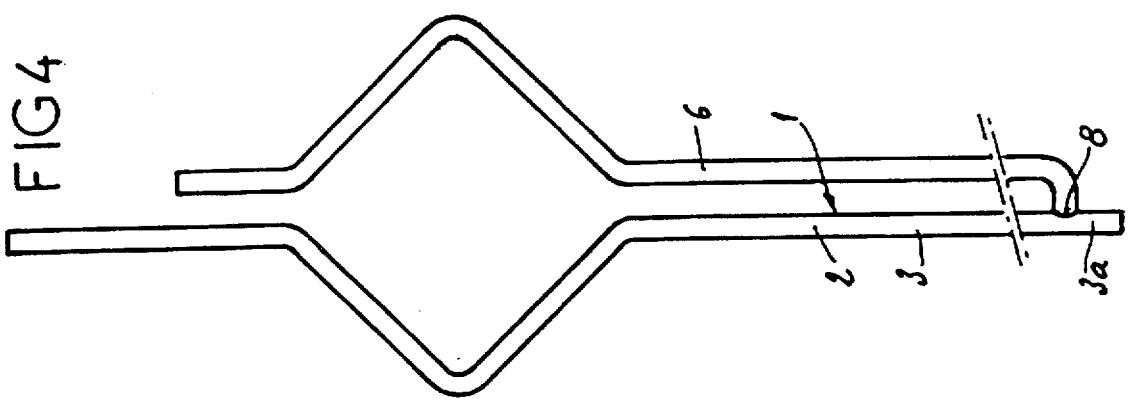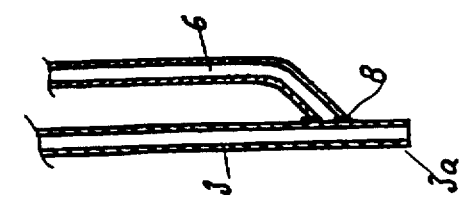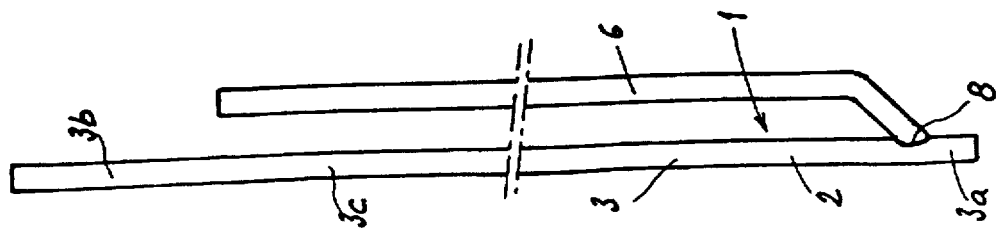

DEVICE FOR WITHDRAWING AND/OR EJECTING A CONTAMINATING MEDIUM, WITH DECONTAMINATION OF THE MEMBER FOR MANIPULATING SAID MEDIUM

The present invention relates to the withdrawing and/or ejecting of a contaminating medium, with decontamination of the member for manipulating the said medium, before or after each withdrawal and/or ejection of the latter.

By "contaminating medium" is understood any medium called upon to be treated or manipulated in any process, procedure or method, for example of analysis, but which is required to be substantially eliminated or disposed of, as undesirable, at one time or another in the said procedure, process or method, and this irrespective of the physical form or presentation of the said medium, for example whether it be a material, substance or sample in liquid or gas form, or two-phase (liquid+gas), or else in powder form, whereupon the said medium can be manipulated like a fluid, especially by suction and/or expulsion. As a consequence of the above definition, "contaminate" and "decontaminate" signify, respectively, bring into contact or supply a contaminating medium into or onto an object, and eliminate or remove the same contaminating medium from the said object. Also, by "inert" will be understood any medium, material or substance devoid of any contaminating medium.

At the forefront of contaminating media of relevance to the present invention are biological media, such as samples of fluid or a bodily specimen, which are liable to contain or be infected with various germs or pathogens, such as viruses, bacteria or other cells. In this case, and for the description below, "contaminating medium" will signify an unsterile medium, and "decontaminate" will signify sterilize.

However, the present invention shall not be limited to sterilization, since many other contaminating media may be of relevance to the invention, for example:

any nucleic substance or matter, such as DNA, manipulated in any technique of molecular biology, or else any organic medium which it is necessary both to manipulate and eliminate, at one time or another, from any process, for example of chemical or biochemical analysis.

However, the common characteristic of all the contaminating media of relevance to the present invention is that they can be destroyed by raising their temperature to a relatively high value, for example exceeding 150° C. Consequently, all the contaminating media of relevance according to the invention can be incinerated or calcined, thereby losing their characteristics or properties which rendered them contaminating.

In various processes or apparatuses for automatic analysis, it is necessary both to withdraw and/or eject a contaminating medium, and to decontaminate the member for manipulating the medium, before or after each withdrawal and/or ejection of the said medium. Thus, in any automated apparatus for bacteriological analysis or detection, in simultaneously treating a plurality of biological samples of differing origins, for example bodily fluid, the manipulating member withdraws each sample from a receptacle containing it, for example a test tube, so as subsequently to eject it with or without dilution, into an analysis kit containing various reagents, themselves contained in various titration wells respectively; in this case, between two elementary operations of withdrawing/ejecting two respectively different samples, it is necessary to employ a sterile manipulating member.

The simplest a priori solution for satisfying the requirement of sterility, necessitated by the manipulation of two successive and respectively different contaminating samples, consists a priori in providing or employing a fresh manipulating member between two elementary withdrawal and/or ejection operations, this manipulating member including a hollow needle for the flow and/or retention of the manipulated contaminating medium. In other words, according to this solution, the manipulating member constitutes a consumable component, which is replaced or discarded after or before each elementary operation of withdrawing and/or ejecting the contaminating medium treated.

This solution involves making or employing manipulating members, especially hollow needles for flow and/or retention, made from a plastic, in order to limit their retail price, and consequently involves the implementation of plastic items which have low rigidity or mechanical strength and are consequently tricky to manipulate in an automated procedure.

Above all, however, such a solution involving the replacement of the manipulating member with each operation of withdrawing and/or ejecting a contaminating medium, proves to be difficult or even impossible to automate, especially given the low intrinsic rigidity, stressed above, of the hollow needles for the flow and/or retention of the contaminating medium. At the very least this automation involves structural or functional complexity of the means contributing thereto.

The subject of the present invention is a solution breaking with the aforesaid approach, and allowing straightforward automation of the decontaminating of the manipulating member of the device for withdrawing and/or ejecting the contaminating medium, whether this device is used in a stand-alone manner, or whether it belongs more generally to an apparatus for treating, especially analysing, one or more samples of contaminating medium.

The present invention is characterized by the cooperating of the following means:

the hollow needle of the member for manipulating the contaminating medium consists essentially of a metal tube, extending from a free so-called active end to an inactive end, determining with the latter a section able to be contaminated and then decontaminated several times, that is to say in a repetitive manner, means for electrical connection are associated with the hollow needle, in order to make an electric current flow therein, and to do so virtually from its active end to its inactive end, that is to say throughout the section of the said needle able to be contaminated, both inside and outside the metal tube, and control means, especially of electrical type, are provided and designed to supply the hollow needle with a predetermined quantity of electrical energy, metered as a function of the electrical characteristics of the metal tube, between a maximum sufficient for decontaminating the needle, in its aforesaid section, both inside and outside the metal tube, and a maximum so as to limit the heating of this same needle and to preserve its integrity, especially its original shape.

Consequently, by virtue of the means of the present invention, the hollow needle and the manipulating member which comprises same become a permanent component of the device for withdrawing and/or ejecting the contaminating medium, which can be used "repeatedly", as it were, this obviously not excluding a periodic changing of this same manipulating member, for reasons of maintenance or wear for example.

In accordance with the technical documents WO-A-92/14096, U.S. Ser. No. 5,300,752, FR-A-2 618 336 and EP-A-0 136 392, it has already been proposed to heat a hypodermic syringe needle by the ohmic effect in order to destroy it completely, especially by melting and/or definitively deforming the metal tube constituting same, whose inside and/or outside had previously been brought into contact with a contaminating medium. In general, according to these documents, an electric current, flowing from the free end to the other end of the said needle, is supplied by any appropriate means to the metal wall and throughout the length of the tube constituting same; this current dissipates thermal energy in the aforesaid tube by the ohmic effect, leading to the melting or complete destruction, especially with definitive deformation, of the syringe needle.

Contrastingly, according to the present invention, the electrical energy supplied to the needle for withdrawing and/or ejecting the contaminating medium is strictly controlled or metered, as a function of the electrical characteristics of the metal tube constituting the said needle, on the one hand to suffice for decontamination of the needle, both inside and outside, and on the other hand to limit the heating and preserve the integrity, including the original shape, of the needle.

According to the invention, it should be noted that the electric current can be supplied to the needle equally well by the inductive effect, by enclosing the hollow needle within an electric circuit designed to make the electric current flow, substantially from the active end to the inactive end of the metal tube constituting the said needle, and determining between them the section able to be contaminated and then decontaminated, repetitively.

Figure 6:
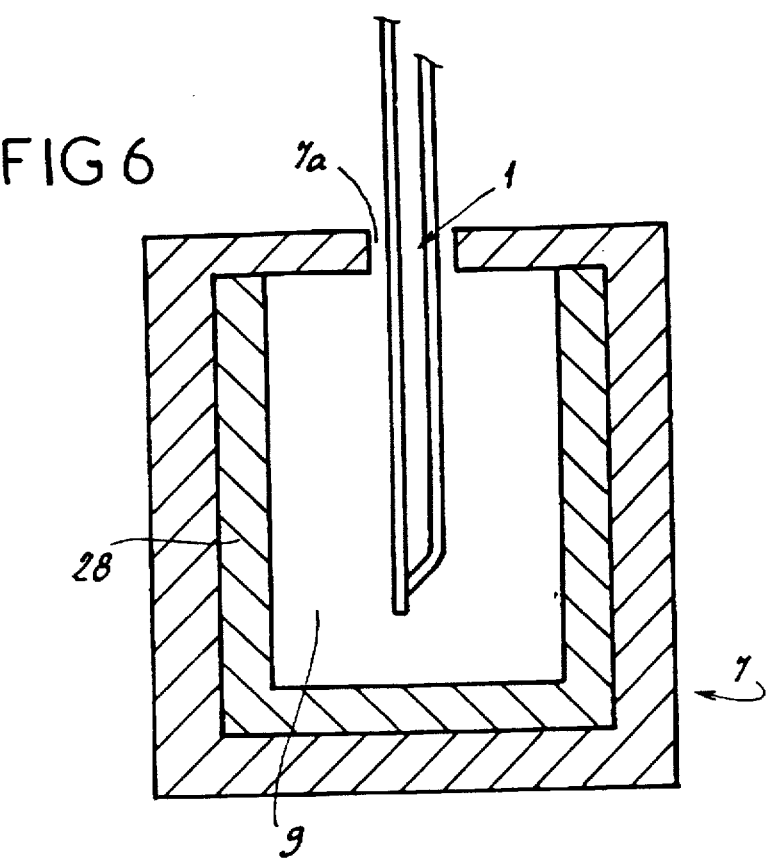

The present invention is now described with reference to the appended drawing in which:

FIG. 1 represents, separately and independently, a device for withdrawing and/or ejecting a contaminating medium, belonging to an apparatus for treating, especially analysing, at least one sample of a contaminating medium, which is otherwise not represented, FIG. 2 represents more particularly the member for manipulating the contaminating medium, such as implemented in the device according to FIG. 1, FIG. 3 represents a sectional view through the manipulating member represented in FIG. 2, FIGS. 4 and 5 represent alternative shapes of the manipulating member represented in FIGS. 2 and 3, FIG. 6 represents a sectional view of the incinerator forming part of the withdrawal and/or ejection device depicted in FIG. 1.

Figure 7:
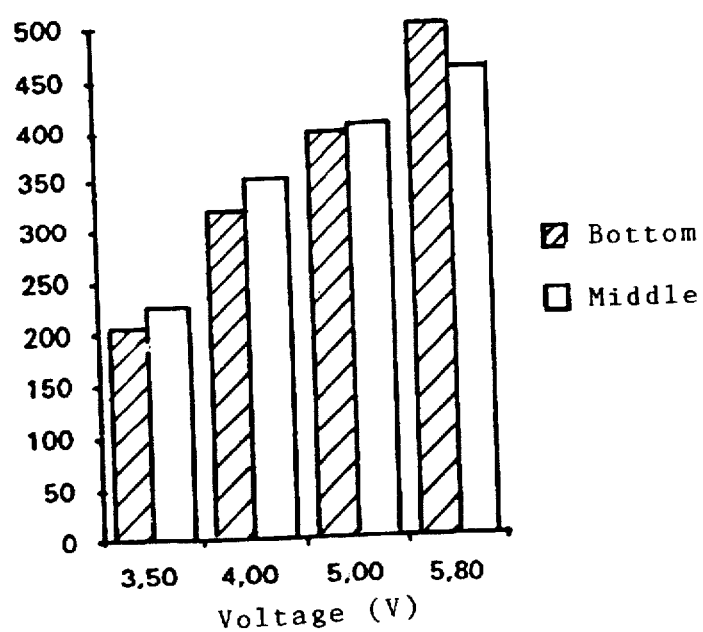

FIG. 7 represents a table illustrating the temperatures reached in °C. at the bottom and in the middle of the hollow needle, respectively versus the electrical voltage applied to the needle.

In accordance with FIG. 1, the device according to the invention makes it possible to withdraw a sample from a contaminating medium, contained in a tube 17, itself supported in a tube holder 16, and then to eject the withdrawn sample into a different tube 18, to which a diluent will also be supplied. This same device makes it possible to decontaminate the manipulating member described below, between two operations of withdrawing and ejecting two samples of respectively different contaminating media, presented one after the other, with regard to the aforesaid manipulating member, for example while presenting a fresh support 16 containing two fresh tubes 17 and 18, the first of which contains a fresh different sample, and the second of which remains empty.

The device represented diagrammatically and in perspective in FIG. 1 comprises in general members or components as follows:

- a member 1 for manipulating the contaminating medium, more particularly represented in FIGS. 2 and 3, comprising a hollow needle 2 for the flow and/or retention of the contaminating medium, and an electrode 6,
- means 5 for electrical connection, associated with the hollow needle 2 and with the electrode 6, in order to make an electric current flow in the said needle,
- an incinerator 7 intended to cooperate with the member 1 for manipulating the contaminating medium, designed or able to incinerate any squirt of the said medium from the hollow needle 2,
- a means 10 for displacing the member 1 for manipulating the contaminating medium, from a position for withdrawing and/or ejecting same, shown by FIG. 1, to a decontaminating position, shown by FIG. 6, in which the manipulating member 1 is arranged inside and at the centre of the incineration vessel 9, according to FIG. 6,
- control means 4, provided and designed in particular to control the quantity of electrical energy supplied to the needle 2, and also to sequence the various steps or operations required in the implementation of the withdrawal and/or ejection device, including passing from the withdrawal and/or ejection position, shown in FIG. 1, to the decontaminating position, shown in FIG. 6, and vice versa.

The hollow needle 2 consists of a metal tube 3 made, for example, of stainless steel or any other appropriate material, such as filled composites, extending from a free end 3a, active in the sense that it is through this end that the contaminating medium is withdrawn and/or ejected, to an inactive end 3b, determining with the previous end a section 3c able to be contaminated and then decontaminated several times, as described below.

The manipulating member 1 also comprises an electrode 6, arranged parallel to the hollow needle 2, and consisting of a metal tube having substantially the same geometrical and electrical characteristics as the metal tube 3 of the hollow needle 2. This electrode 6 is in electrical continuity with the metal tube, in a region 8 of linkage with the electrode, adjacent to the active end 3a of the needle 2; this region of linkage is shut off by a metal insert so as to preserve the leaktightness of the tube 3 in relation to the hollow electrode 6.

Other shapes of manipulating members are shown in FIGS. 4 and 5 respectively, providing an expansion loop in both the metal tube 3 and the electrode 6, the configuration of the metal tube 3 moreover making it possible to avoid a reflux of the contaminating medium.

The means 5 for electrical connection include two electrical contacts 51 and 52, respectively with the inactive end 3b of the hollow needle 2, and with the end of the electrode 6, away from the linkage region 8, this enabling an electric current to be made to flow in the hollow needle 2, substantially from its active end 3a, or in a manner adjacent to this end, to its inactive end 3b, that is to say virtually throughout the section 3c. In this manner also, virtually the whole electrode 6, situated in terms of level in the section 3c, is also traversed by the electric current for decontaminating the hollow needle 2.

As represented in FIG. 6, the incinerator 7 comprises a hot wall 28, brought to temperature by means which are not represented, such as an electrical resistor, this wall determining an incineration vessel 9, around and at some distance from the manipulating member 1, when the latter has penetrated into the incinerator 7 via its upper opening 7a. The temperature in the incineration vessel 9 is controlled or adjusted so as to allow the incineration of any squirt of the contaminating medium from the end or from the outside face of the metal tube 3 of the hollow needle 2.

The means 10 for displacing the member 1 for manipulating the contaminating medium comprises a pivoting arm 11, mounted at the upper end of a stand 19, this arm being able to pass from the withdrawal and/or ejection position, shown in FIG. 1, to the decontaminating position, shown in FIG. 6, as instructed by the control means 4. Mounted and carried at the free end of the arm 11 is a member 12 for vertical displacement of the manipulating member 1, consisting, in a manner not represented, of a rack driven by an electric motor. In the decontaminating position of FIG. 6, the opening 7a in the incinerator 7 is plumb with this member 12 for vertical displacement.

As represented diagrammatically in FIG. 1, the end 3b of the hollow needle 2 of the member 1 for manipulating the contaminating medium is connected, by one and the same pipe 20, on the one hand to a source 13 for sucking up and/or expelling the contaminating medium, and on the other hand to a source 14 of a diluent of the contaminating medium, which is able to be ejected by the needle 2, and by a pipe 21 to a source 15 of a pressurized inert gas, which can be sucked up or expelled by the needle 2.

The control means 4 is designed to sequence at least two elementary operations, chosen from the following operations, as a function of the procedure or protocol for withdrawal and/or ejection, with decontamination, adopted by the user:

sucking up and/or expelling, with the source 13, the contaminating medium via the hollow needle 2, ejecting by means of the source 15 a flux of inert gas through the hollow needle 2, expelling through the hollow needle 2 a stream 14 of a diluent, and passing from the position of withdrawal and/or the position of ejection of the contaminating medium to the decontaminating position, and vice versa.

These same control means enable a predetermined quantity of electrical energy, metered as a function of the electrical characteristics of the tube 3 and of the electrode 6, to be supplied both to the hollow needle 2 and also to the electrode 6, on the one hand so as to suffice for the decontamination of the needle 2 and of the electrode 6, both inside and outside, and on the other hand so as to limit heat-up and preserve the integrity, including the original shape, of the needle 2 and of the electrode 6.

By virtue of the arrangement of the electrode 6, with respect to the hollow needle 3, more particularly shown in FIG. 3, in order in particular to decontaminate the hollow needle 2, the latter is therefore enclosed within an electrical circuit enabling an electric current to be made to flow virtually from the active end 3a of the tube 3 to the inactive end 3b of the needle 2, separated from the end 3a by a distance determining the section 3c of the needle 2 able to be contaminated and then decontaminated repetitively; indeed, during the decontamination phase, the electric current flows from the linkage region 8, adjacent to the active end 3a, to the inactive end 3b of the needle 2. During the phase of heating the needle 2 in order to decontaminate it, the said needle is arranged inside the incineration vessel 9, whose hot wall 28 arranged around and some distance from the needle 2 makes it possible to incinerate any squirt of contaminating medium, from the active end 3a and/or from the outside face of the metal tube 3 and/or from the outside face of the electrode 6.

A withdrawal and/or ejection device according to the invention has been tried out with regard to its sterilization performance.

The hollow needle 2 consists of a stainless steel tube, having a useful length of for example about 100 mm, preferably 125 mm, an external section of between 0.5 and 3 mm, in particular about 2 mm. The electrode 6 consists of the same metal tube, having a useful length similar to that of the metal tube 3, about 100 mm for example.

The step of sterilization or decontamination in the incinerator is made up of the following phases:

blowing of inert air through the needle 2, without heating; heating by ohmic effect, with blowing of inert air; and blowing of inert air without heating; the whole in 6 seconds blowing of inert air, for 3 seconds, in order to cool the needle 2 and the electrode 6.

The table in FIG. 7 gives the temperatures reached in °C., respectively at the bottom and in the middle of the hollow needle 2, versus the electrical voltage in V applied to the latter.

Next, retaining the same heating time for the hollow needle 2, of between about 1 and 5 seconds, and preferably between 2 and 3 seconds, for an electrical voltage applied to the needle of 4 V, the sterilization performance of the device according to the invention is tried out with regard to four microorganisms, namely *E. coli, P. aeruginosa, C. albicans, S. epidermidis*. To do this, the following protocol is used:

the needle 2 is contaminated with a sample of $6.10^8$ cells/ml of each microorganism next, the needle 2 is sterilized in accordance with the step defined above, and at the end of the sterilization step, a volume of 2.1 ml of an inert (aseptic) diluent is passed through the active end 3a this volume is divided into fractions of 0.3 ml, respectively inoculating 7 dishes containing a blood-agar nutrient after incubation overnight at a temperature of between 30° and 42° C., preferably 37° C., the tested microorganism is identified and counted a positive control (diluent with the relevant microorganism) and a reference control (the diluent alone) are employed a first series of 10 assays and a second series of 5 assays are performed for each microorganism.

Under these conditions, after sterilization, no contamination with the tested microorganism was observed.

We claim:

1. A method of decontaminating a hollow needle, comprising:

supplying electric current to the hollow needle subsequent to contact with a contaminating medium in order to heat the hollow needle; and controlling an amount of electric current supplied to the hollow needle based on electrical conductivity characteristics of the hollow needle, such that a sufficient amount of electric current is supplied to the hollow needle to decontaminate the hollow needle both inside and outside while preserving the integrity and shape of the hollow needle;

whereby the hollow needle can repeatedly be used with one or more contaminating medium and be decontaminated after such use.

2. A method of decontaminating a hollow needle according to claim 1, wherein supplying electric current includes heating the hollow needle pursuant to the Ohmic effect by allowing current to flow over a length of the hollow needle.

3. A method of decontaminating a hollow needle according to claim 1, wherein supplying electric current includes supplying electric current through the inductive effect.

4. A method of decontaminating a hollow needle according to claim 1, wherein supplying electric current includes allowing electric current to flow from an active end of the hollow needle to an inactive end of the hollow needle, the active and inactive ends defining therebetween a section of the hollow needle subject to decontamination.

5. A method of decontaminating a hollow needle according to claim 1, wherein supplying electric current includes allowing electric current to flow from a region adjacent an active end of the hollow needle to an inactive end of the hollow needle.

6. A method of decontaminating a hollow needle according to claim 1, further comprising positioning the hollow needle within an incineration vessel while supplying the electric current to the hollow needle, and heating an interior of the incineration vessel to incinerate any volume of the contaminating medium emitted from the hollow needle and/or disposed on an exterior surface of the hollow needle.

7. An apparatus for decontaminating a hollow needle, comprising:

a hollow needle for withdrawing a medium that can contaminate said needle, ejecting a medium that can contaminate said needle, or both, the hollow needle having an active end and an inactive end, the active and inactive ends defining therebetween a section of the hollow needle subject to contact with the contaminating medium;

a power supply that supplies electric current to the hollow needle subsequent to contact with the contaminating medium; and a controller that controls the amount of electric current supplied to the hollow needle, based on electrical conductivity characteristics of the hollow needle, such that a sufficient amount of electric current is supplied to the hollow needle to decontaminate the hollow needle both inside and outside while preserving the integrity and shape of the hollow needle;

whereby the hollow needle can repeatedly be used with one or more contaminating medium and be decontaminated after each such use.

8. An apparatus for decontaminating a hollow needle according to claim 7, wherein the power supply includes an electrode connected to the hollow needle at a region adjacent the active end of the hollow needle such that electric current is transferable between the electrode and the hollow needle.

9. An apparatus for decontaminating a hollow needle according to claim 8, wherein a section of the electrode is parallel to a section of the hollow needle.

10. An apparatus for decontaminating a hollow needle according to claim 8, wherein the electrode has substantially the same geometric dimensions and electrical characteristics as the hollow needle.

11. An apparatus for decontaminating a hollow needle according to claim 7, further comprising an incinerator including a hot wall that defines an incineration vessel for incinerating any volume of the contaminating medium emitted from the hollow needle, disposed on an exterior surface of the hollow needle, or both, and a means for displacing the hollow needle from a position in fluid communication with the contaminating medium to a decontaminating position in which the hollow needle is disposed within the incineration vessel.

12. An apparatus for decontaminating a hollow needle according to claim 11, wherein the means for displacing the hollow needle includes an arm pivotable from the position in fluid communication with the contaminating medium to the decontaminating position.

13. An apparatus for decontaminating a hollow needle according to claim 12, wherein the means for displacing the hollow needle further includes a vertical displacement assembly that moves the hollow needle vertically.

14. An apparatus for decontaminating a hollow needle according to claim 7, further comprising means for withdrawing and ejecting the contaminating medium via the hollow needle, the means for withdrawing and ejecting being connected to the inactive end of the hollow needle.

15. An apparatus for decontaminating a hollow needle according to claim 7, further comprising a source of pressurized inert gas, the source of pressurized inert gas being connected to the inactive end of the hollow needle.

16. An apparatus for decontaminating a hollow needle according to claim 7, further comprising a source of diluent of the contaminating medium, the source of diluent of the contaminating medium connected to the inactive end of the hollow needle.

17. An apparatus for decontaminating a hollow needle according to claim 7, further comprising an incinerator, and wherein the controller includes an actuator that actuates at least two operations selected from the group consisting of a sampling operation that includes withdrawing the contaminating medium through the hollow needle, ejecting the contaminating medium through the hollow needle, or both; ejecting a volume of inert gas through the hollow needle; ejecting a volume of diluent of the contaminating medium through the hollow needle; and moving the hollow needle between a position in fluid communication with the contaminating medium and a decontaminating position in which the hollow needle is disposed within the incineration vessel.

* * * * *